US009688733B2

(12) United States Patent
Tamai et al.

(10) Patent No.: US 9,688,733 B2
(45) Date of Patent: Jun. 27, 2017

(54) METHOD FOR TREATING SPINAL CORD INJURY USING HMGB1 FRAGMENT (71) Applicants: GENOMIX CO., LTD, Osaka (JP); OSAKA UNIVERSITY, Osaka (JP)

(72) Inventors: Katsuto Tamai, Osaka (JP); Takehiko Yamazaki, Osaka (JP); Wenhao Cui, Osaka (JP)

(73) Assignees: GENOMIX CO., LTD., Osaka (JP); OSAKA UNIVERSITY, Osaka (JP)

( * ) Notice: Subject to any disclaimer, the term of this patent is extended or adjusted under 35 U.S.C. 154(b) by 0 days.

(21) Appl. No.: 14/436,920

(22) PCT Filed: Oct. 24, 2013

(86) PCT No.: PCT/JP2013/078759
§ 371 (c)(1),
(2) Date: Apr. 20, 2015

(87) PCT Pub. No.: WO2014/065348
PCT Pub. Date: May 1, 2014

(65) Prior Publication Data
US 2015/0274792 A1    Oct. 1, 2015

(30) Foreign Application Priority Data
Oct. 25, 2012   (JP) ................................ 2012-235786

(51) Int. Cl.
A61K 38/00    (2006.01)
A61K 38/16    (2006.01)
C07K 14/47    (2006.01)

(52) U.S. Cl.
CPC .............. *C07K 14/47* (2013.01); *A61K 38/16* (2013.01)

(58) Field of Classification Search
None
See application file for complete search history.

(56) References Cited

U.S. PATENT DOCUMENTS

| | | | |
|---|---|---|---|
| 3,896,810 A | 7/1975 | Akiyama | |
| 5,661,127 A | 8/1997 | Bhatnagar et al. | |
| 5,851,986 A | 12/1998 | Takada et al. | |
| 5,902,799 A | 5/1999 | Herrmann et al. | |
| 2002/0058019 A1 | 5/2002 | Berenson et al. | |
| 2003/0003482 A1 | 1/2003 | Halle et al. | |
| 2003/0060410 A1 | 3/2003 | Tracey et al. | |
| 2004/0031072 A1 | 2/2004 | La Rosa et al. | |
| 2004/0053841 A1 | 3/2004 | Tracey et al. | |
| 2004/0191246 A1 | 9/2004 | Connelly et al. | |
| 2004/0242481 A1 | 12/2004 | Bianchi et al. | |
| 2004/0265971 A1 | 12/2004 | Sato et al. | |
| 2005/0014255 A1 | 1/2005 | Tang et al. | |
| 2005/0260174 A1 | 11/2005 | Fraser et al. | |
| 2006/0035851 A1 | 2/2006 | Bianchi et al. | |
| 2006/0111287 A1 | 5/2006 | Bianchi | |
| 2006/0127373 A1 | 6/2006 | Son et al. | |
| 2006/0281674 A1 | 12/2006 | Tessier et al. | |
| 2007/0154529 A1 | 7/2007 | Bullerdiek | |
| 2009/0053277 A1 | 2/2009 | Nagaya et al. | |
| 2009/0062187 A1 | 3/2009 | Bianchi et al. | |
| 2009/0202500 A1 | 8/2009 | Tamai et al. | |
| 2009/0280488 A1 | 11/2009 | Okazawa | |
| 2011/0091928 A1 | 4/2011 | Tamai et al. | |
| 2011/0097309 A1 | 4/2011 | Tamai et al. | |
| 2011/0104803 A1 | 5/2011 | Tamai et al. | |
| 2012/0251510 A1 | 10/2012 | Tamai et al. | |
| 2014/0206619 A1 | 7/2014 | Tamai et al. | |
| 2015/0273017 A1 | 10/2015 | Tamai et al. | |

FOREIGN PATENT DOCUMENTS

| | | |
|---|---|---|
| AU | 2003228099 A1 | 1/2004 |
| AU | 2004203732 A1 | 7/2004 |
| CA | 2325226 | 5/2001 |
| CA | 2512512 A1 | 7/2004 |
| CA | 2636788 | 5/2008 |
| CN | 1516739 A | 7/2004 |
| CN | 1671742 A | 9/2005 |
| CN | 101374538 A | 2/2009 |
| CN | 102076350 A | 5/2011 |
| CN | 102443064 | 5/2012 |
| CN | 102711777 A | 10/2012 |
| EP | 0791601 A2 | 8/1997 |
| EP | 1114862 A1 | 7/2001 |
| EP | 1459759 A1 | 9/2004 |
| EP | 2 039 367 | 3/2009 |
| EP | 2055308 A1 | 5/2009 |
| EP | 2284255 A1 | 2/2011 |
| EP | 2301559 A1 | 3/2011 |
| JP | H 9-227403 | 9/1997 |
| JP | 2001321434 A | 11/2001 |
| JP | 2003505506 A | 2/2003 |
| JP | 2005508913 A | 4/2005 |

(Continued)

OTHER PUBLICATIONS

Esposito et al., 2009, J. Pineal Res., 46:79-86.*
Kikuchi et al., 2011, Exp. Therap. Med., 2:767-70.*
Kawabata et al., 2012, Spine, 36(25):2122-9.*
Mansbridge, Jonathan, "Skin Tissue Engineering," *J. Biomater. Sci. Polymer Ed.*, Aug. 1, 2008, 19(8):955-968.
Chamberlain, Giselle et al., "Concise Review: Mesenchymal Stem Cells: Their Phenotype, Differentiation Capacity, Immunological Features, and Potential for Homing," *Stem Cells* 2007; 25:2739-2749.
Kessler, Michael W. et al., "Tissue Engineering and Cartilage," *Organogenesis*, Jan. 2008; 4(1):28-32.
Lanza, Robert et al., and Arnold Caplan, "Essentials of Stem Cell Biology—Chapter 27, Mesenchymal Stem Cells," *Elsevier Academic Press*, 2006, pp. 205-210.
De Souza, A.W.S. et al., "HMGB1 in Vascular Diseases: Its Role in Vascular Inflammation and Atherosclerosis," *Autoimmunity Reviews*, 2012, 11:909-917.

(Continued)

*Primary Examiner* — Olga N Chernyshev
(74) *Attorney, Agent, or Firm* — Saliwanchik, Lloyd & Eisenschenk (57) ABSTRACT

Fragment peptides having a proper length, which consists of a portion of the HMGB1 protein were synthesized, and the peptides were confirmed to show therapeutic effects on injury of the spinal cord.

2 Claims, 6 Drawing Sheets

(56) References Cited

FOREIGN PATENT DOCUMENTS

| | | |
|---|---|---|
| JP | 2005-512507 | 5/2005 |
| JP | 2005537253 A | 12/2005 |
| JP | 2006124389 A | 5/2006 |
| JP | 2006517537 A | 7/2006 |
| JP | 2006523085 A | 10/2006 |
| JP | 2007-320919 | 12/2007 |
| JP | 2008507505 A | 3/2008 |
| KR | 20090078304 A | 7/2009 |
| RU | 2005102593 A | 10/2005 |
| RU | 2 410 125 C2 | 1/2011 |
| WO | WO 01/08683 A1 | 2/2001 |
| WO | WO 02/074337 A1 | 9/2002 |
| WO | WO 02/088181 A2 | 11/2002 |
| WO | WO 02/092004 A2 | 11/2002 |
| WO | WO 03/026691 A2 | 4/2003 |
| WO | WO 03/043651 A1 | 5/2003 |
| WO | WO 2004/004763 | 1/2004 |
| WO | WO 2004/004770 A1 | 1/2004 |
| WO | WO 2004/044001 A2 | 5/2004 |
| WO | WO 2004/046345 A2 | 6/2004 |
| WO | WO 2004/061456 A2 | 7/2004 |
| WO | WO 2005/025604 A2 | 3/2005 |
| WO | WO 2005/074984 A1 | 8/2005 |
| WO | WO 2006/008779 A1 | 1/2006 |
| WO | WO 2006/010628 A1 | 2/2006 |
| WO | WO 2006/024547 A2 | 3/2006 |
| WO | WO 2006/047820 A1 | 5/2006 |
| WO | WO 2006/077614 A1 | 7/2006 |
| WO | WO 2006/080434 A1 | 8/2006 |
| WO | WO 2006/100651 A1 | 9/2006 |
| WO | WO 2006/114805 A2 | 11/2006 |
| WO | WO 2007/015546 | 2/2007 |
| WO | WO 2007/031100 A1 | 3/2007 |
| WO | WO 2007-130725 A | 11/2007 |
| WO | WO 2008/018641 A1 | 2/2008 |
| WO | WO 2008/053892 | 5/2008 |
| WO | WO 2009/133939 | 11/2009 |
| WO | WO 2009/133940 | 11/2009 |
| WO | WO 2009/133943 | 11/2009 |
| WO | WO 2011/046570 | 4/2011 |
| WO | WO 2011/052668 A1 | 5/2011 |
| WO | WO 2012/147470 A1 | 11/2012 |
| WO | WO 2014/065347 A1 | 5/2014 |

OTHER PUBLICATIONS

Zhou, Xiaoya et al., "Exogenous High-Mobility Group Box 1 Protein Injection Improves Cardiac Function after Myocardial Infarction: Involvement of Wnt Signaling Activation," *Journal of Biomedicine and Biotechnology*, 2012, vol. 2012, pp. 1-5.

Cole, John Sterling, "Pharmacologic Mobilization of Mesenchymal Stem Cells for Enhanced Bone Formation," *Colby College, Rush University*, 2009; UMI No. 1466383, pp. 1-82.

Kirov, Sergei A. et al., "In Vivo 2-Photon Microscopy Reveals G-CSF Enhanced Mobilization and Targeting of Neo-Endogenous Bone Marrow Stromal Cells to Stroke Injury Sites," *Stroke*, Apr. 2009, 40(4):1-2, e133, Abstract No. 107.

Straino, Stefania et al., "High-Mobility Group Box 1 Protein in Human and Murine Skin: Involvement in Wound Healing," *Journal of Investigative Dermatology*, 2008, 128:1545-1553.

"Isolating Culture and Induced Differentiation of Marrow Mesenchyma Stem Cells," *Principles and Protocols of Tissue Engineering*, Jun. 2004, pp. 277-278.

Alden, Tord D. et al. "In Vivo Endochondral Bone Formation Using a Bone Morphogenetic Protein 2 Adenoviral Vector," *Human Gene Therapy*, Sep. 1, 1999, 10:2245-2253.

Bittira, Bindu et al. "Mobilization and homing of bone marrow stromal cells in myocardial infarction," *European Journal of Cardio-thoracic Surgery*, Sep. 2003, 24:393-398.

Castro, Raymond F. et al. "Failure of Bone Marrow Cells to Transdifferentiate into Neural Cells in Vivo," *Science*, Aug. 23, 2002, 297:1299.

Charoonpatrapong, Kanokwan et al. "HMGB1 Expression and Release by Bone Cells," *Journal of Cellular Physiology*, 2006, 207:480-490.

Chen, Xiaoguang et al., "Human Bone Marrow Stromal Cell Cultures Conditioned by Traumatic Brain Tissue Extracts: Growth Factor Production," *Journal of Neuroscience Research*, Sep. 1, 2002, 69:687-691.

Chen, Y. et al. "Coaxing bone marrow stromal mesenchymal stem cells towards neuronal differentiation: progress and uncertainties," *Cellular and Molecular Life Sciences*, Jul. 2006, 63:1649-1657.

Chopp, Michael et al., "Treatment of neural injury with marrow stromal cells," *The Lancet Neurology*, Jun. 2002, 2:92-100.

Chou, Denise K. H. et al., "Identity of nuclear high-mobility-group protein, HMG-1, and sulfoglucuronyl carbohydrate-binding protein, SBP-1, in brain," *Journal of Neurochemistry*, Apr. 2001, 77:120-131.

Degryse, Bernard et al., "The High Mobility Group (HMG) Boxes of the Nuclear Protein HMG1 Induce Chemotaxis and Cytoskeleton Reorganization in Rat Smooth Muscle Cells," *The Journal of Cell Biology*, Mar. 19, 2001, 152(6):1197-1206.

Delarosa, Olga et al., "Modulation of Adult Mesenchymal Stem Cells Activity by Toll-Like Receptors: Implications on Therapeutic Potential," *Mediators of Inflammation*, 2010, Article ID 865601, pp. 1-9.

Dong, Yingying et al., "HMGB1 Protein Does Not Mediate the Inflammatory Response in Spontaneous Spinal Cord Regeneration," *The Journal of Biological Chemistry*, Jun. 21, 2013, 288(25):18204-18218.

Eckert, Richard L. et al., "S100 Proteins in the Epidermis," *The Journal of Investigative Dermatology*, Jul. 2004, 123:23-33.

Ehrchen, Jan M. et al., "The endogenous Toll-like receptor 4 agonist S100A8/S100A9 (calprotectin) as innate amplifier of infection, autoimmunity, and cancer," *Journal of Leukocyte Biology*, Sep. 2009, 86:557-566.

Forte, Giancarlo et al., "Hepatocyte Growth Factor Effects on Mesenchymal Stem Cells: Proliferation, Migration, and Differentiation," *Stem Cells*, Jan. 2006, 24:23-33.

Fujii, Makiko et al., "Roles of Bone Morphogenetic Protein Type 1 Receptors and Smad Proteins in Osteoblast and Chondroblast Differentiation," *Molecular Biology of the Cell*, Nov. 1999, 10:3801-3813.

Granero-Molto, Froilan et al., "Role of mesenchymal stem cells in regenerative medicine: application to bone and cartilage repair," *Expert Opinion on Biological Therapy*, Mar. 2008, 8(3):255-268.

Gudjonsson, Johann E. et al. "Chapter 18—Psoriasis," *Fitzpatrick's Dermatology in General Medicine*, 8th edition, 2012, pp. 197-217.

Gueukdjian, S. A. "Intra-Arterial Injections in the Treatment of Peripheral Vascular Disease," *Postgrad Medicine Journal*, Jan. 1955, 31:30-31.

Harris, Helena Erlandsson of al., "Alarmin(g) news about danger," *EMBO reports*, Jul. 21, 2006, 7(8):774-778.

Harris, Helena Erlandsson et al., "The nuclear protein HMGB1 as a proinflammatory mediator," *European Journal of Immunology*, Jun. 2004, 34:1503-1512.

Heil, Matthias et al., "An engineered heparin-binding form of VEGF-E (hbVEGF-E)," *Angiogenesis*, 2003, 6:201-211.

Hiratsuka, Sachie et al., "Tumour-mediated upregulation of chemoattractants and recruitment of myeloid cells predetermines lung metastasis," *Nature Cell Biology*, Dec. 2006, 8(12):1369-1375.

Huttunen, Henri J. et al., "Receptor for Advanced Glycation End Products-binding COOH-terminal Motif of Amphoterin Inhibits Invasive Migration and Metastasis," *Cancer Research*, Aug. 15, 2002, 62:4805-4811.

Institutional Animal Care and Use Committee (IACUC), "Blood Collection: The Mouse," *University of California, San Francisco*, May 2014, accessed from: iacuc.usfc.edu/Policies/BloodCollectionMice.doc.

Instruction Manual, "HiTrap Chelating HP," *Amersham Biosciences*, 2003, 18-1134-78 AD, pp. 1-6.

Jansen, Jan et al., "Transplantation of hematopoietic stem cells from the peripheral blood," *Journal of Cellular and Molecular Medicine*, 2005, 9(1):37-50.

(56) References Cited

OTHER PUBLICATIONS

Jayaraman, Lata et al., "High mobility group protein-1 (HMG-1) is a unique activator of?p53," *Genes & Development*, Feb. 1998, 12:462-472.
Jiang, Yuehua et al., "Pluripotency of mesenchymal stem cells derived from adult marrow," *Nature*, Jul. 4, 2002, 418:41-49.
Kassis, I. et al., "Isolation of mesenchymal stem cells from G-CSF-mobilized human peripheral blood using fibrin microbeads," *Bone Marrow Transplantation*, May 2006, 37:967-976.
Kern, Susanne et al., "Comparative Analysis of Mesenchymal Stem Cells from Bone Marrow, Umbilical Cord Blood, or Adipose Tissue," *Stem Cells*, May 2006, 24:1294-1301.
Kikuchi, Kiyoshi et al., "HMGB1 as a therapeutic target in spinal cord injury: A hypothesis for novel therapy development (Review)," *Experimental and Therapeutic Medicine*, 2011, 2:767-770.
Kim, Sang-Soo et al., "Skin Regeneration Using Keratinocytes and Dermal Fibroblasts Cultured on Biodegradable Microspherical Polymer Scaffolds," *Journal of Biomedical Materials Research Part B: Applied Biomaterials*, 2005, 75B:369-377.
Kitahara, Tatsuro et al., "High-mobility group box 1 restores cardiac function after myocardial infarction in transgenic mice," *Cardiovascular Research*, Jun. 2008, 80:40-46.
Koc, On et al., "Mesenchymal stem cells: heading into the clinic," *Bone Marrow Transplantation*, 2001, 27:235-239.
Kohno, Takashi et al., "High Mobility Group Box 1 Protein is associated with Post-Infarction Healing Process and Left Ventricular Remodeling," *Circulation Journal*, 2008, 72(Suppl 1):510-511.
La Rosa, T.J. et al., "Glycine max protein SEQ ID No:211221," *Geneseq Accession No.* AFQ20044, Oct. 18, 2007, XP-002730227.
Laflamme, Michael A. et al., "Regenerating the heart," *Nature Biotechnology*, Jul. 2005, 23(7):845-856.
Li, S. et al., "Nonviral gene therapy: promises and challenges," *Gene Therapy*, 2000, 7:31-34.
Limana, Federica et al., "Exogenous High-Mobility Group Box 1 Protein Induces Myocardial Regeneration After Infarction via Enhanced Cardiac C-Kit+Cell Proliferation and Differentiation," *Circulation Research*, Sep. 15, 2005, 97:e73-e83.
Lin, Siang-Yo et al., "The isolation of novel mesenchymal stromal cell chemotactic factors from the conditioned medium of tumor cells," *Experimental Cell Research*, Aug. 8, 2008, 314:3107-3117.
Liotta, Francesco et al., "Toll-Like Receptors 3 and 4 Are Expressed by Human Bone Marrow-Derived Mesenchymal Stem Cells and Can Inhibit Their T-Cell Modulatory Activity by Impairing Notch Signaling," *Stem Cells*, 2008, 26:279-289.
Liu, Ke-Xin et al., "Human Placental Extract Stimulates Liver Regeneration in Rats," *Biological and Pharmaceutical Bulletin*, 1998, 21(1):44-49.
Lonza BenchGuides, "Poietics Human Mesenchymal Stem Cells & Media," *Lonza Walkersville, Inc.*, 2008, (Document # T S-Pt-212-7 04/08).
Maruyama, Ikuro. "Inflammation and HMGB1/RAGE system," *Kekkan Igaku*, 2005, 6(5):519-25.
Matsumoto, Kunio et al., "Up-Regulation of Hepatocyte Growth Factor Gene Expression by Interleukin-1 in Human Skin Fibroblasts," *Biochemical and Biophysical Research Communications*, Oct. 15, 1992, 188(1):235-243.
Meng, Erhong et al., "High Mobility Group Box 1 Protein Inhibits the Proliferation of Human Mesenchymal Stem Cells and Promotes Their Migration and Differentiation along Osteoblastic Pathway," *Stem Cells and Development*, 2008, 17:805-814.
Meng, Er-Hong et al., "HMGB1 induces migration of human bone marrow-derived mesenchymal stem cells," *Bulletin of the Academy of Military Medical Sciences*, Jun. 2006, 30(3):213-216.
Mistry, A.R. et al., "Recombinant HMG1 Protein Produced in *Pichia pastoris*: A Nonviral Gene Delivery Agent," *BioTechniques*, Apr. 1997, 22:718-729.
Mori, Taisuke et al., "Stem Cells / ES cells—Mesenchymal Stem Cells—Human Bone Marrow Derived Mesenchymal Stem Cells," *Saisei Iryou—Regenerative Medicine*, 2005, 4(3):421-9, 351.

Muhammad, Sajjad et al., "The HMGB1 Receptor RAGE Mediates Ischemic Brain Damage," *The Journal of Neuroscience*, Nov. 12, 2008, 28(46):12023-12031.
Nakamura, Koji et al., "p38 Mitogen-Activated Protein Kinase Functionally Contributes to Chondrogenesis Induced by Growth/Differentiation Factor-5 in ATDC5 Cells," *Experimental Cell Research*, 1999, 250:351-363.
Opitz, Christiane A. et al., "Toll-Like Receptor Engagement Enhances the Immunosuppressive Properties of Human Bone Marrow-Derived Mesenchymal Stem Cells by Inducing Indoleamine-2,3-dioxygenase-1 via Interferon-β and Protein Kinase R," *Stem Cells*, 2009, 27:909-919.
Otsuru, Satoru et al., "BMP-2 mobilizes robust bone marrow mesenchymal progenitor cells to the circulating blood in bone regeneration," *The 28th Annual Meeting of the Molecular Biology Society of Japan*, Dec. 2005, 733:3P-1012.
Ozaki, Yoshie et al., "Comprehensive Analysis of Chemotactic Factors for Bone Marrow Mesenchymal Stem Cells," *Stem Cells and Development*, 2007, 16:119-129.
Palumbo, Roberta et al., "Cells migrating to sites of tissue damage in response to the danger signal HMGB1 require NF-κB activation," *The Journal of Cell Biology*, Oct. 8, 2007, 179(1):33-40.
Palumbo, Roberta et al., "High mobility group box 1 protein, a cue for stem cell recruitment," *Biochemical Pharmacology*, Apr. 19, 2004, 68:1165-1170.
Paul, S.R. et al., "Stromal Cell-Associated Hematopoiesis: Immortalization and Characterization of a Primate Bone Marrow-Derived Stromal Cell Line," *Blood Journal*, Apr. 15, 1991, 77(8):1723-1733.
Pevsner-Fischer, Meirav et al., "Toll-like receptors and their ligands control mesenchymal stem cell functions," *Blood*, Feb. 15, 2007, 109(4):1422-1432.
Pittenger, Mark F. et al., "Multilineage Potential of Adult Human Mesenchymal Stem Cells," *Science*, Apr. 2, 1999, 284:143-147.
Popovic, Karin et al., "Increased Expression of the Novel Proinflammatory Cytokine High Mobility Group Box Chromosomal Protein 1 in Skin Lesions of Patients With Lupus Erythematosus," *Arthritis & Rheumatism*, Nov. 2005, 52(11):3639-3645.
Pusterla, Tobias et al., "High mobility group B2 is secreted by myeloid cells and has mitogenic and chemoattractant activities similar to high mobility group B1," *Autoimmunity*, Apr. 2009, 42(4):308-310.
Raicevic, Gordana et al., Inflammation modifies the pattern and the function of Toll-like receptors expressed by human mesenchymal stromal cells, *Human Immunology*, Jan. 6, 2010, 71:235-244.
Robinson, Matthew J. et al., "The S100 Family Heterodimer, MRP-8/14, Binds with High Affinity to Heparin and Heparan Sulfate Glycosaminoglycans on Endothelial Cells," *The Journal of Biological Chemistry*, Feb. 1, 2002, 277(5):3658-3665.
Ryckman, Carle et al., "Proinflammatory Activities of S100: Proteins S100A8, S100A9, and S100A8/A9 Induce Neutrophil Chemotaxis and Adhesion," *The Journal of Immunology*, Mar. 15, 2003, 170(6):3233-3242.
Sasaki, Mikako et al., "Mesenchymal Stem Cells Are Recruited into Wounded Skin and Contribute to Wound Repair by Transdifferentiation into Multiple Skin Cell Type[1]," *The Journal of Immunology*, Feb. 15, 2008, 180(4):2581-7.
Schäffer, Michael R. et al., "Wound Fluid Inhibits Wound Fibroblast Nitric Oxide Synthesis," *Journal of Surgical Research*, Nov. 2004, 122(1):43-48.
Schön, Michael P. et al., "Psoriasis," *The New England Journal of Medicine*, May 5, 2005, 352(18):1899-1912.
Shibata, Futoshi et al., "Fibroblast Growth-Stimulating Activity of S100A9 (MRP-14)," *European Journal of Biochemistry*, Jun. 2004, 271(11):2137-2143.
Shing, Y et al., "Heparin Affinity: Purification of a Tumor-Derived Capillary Endothelial Cell Growth Factor," *Science*, Mar. 23, 1984, 223(4642):1296-1299.
Somia, Nikunj et al., "Gene Therapy: Trials and Tribulations," *Nature Reviews: Genetics*, Nov. 2000, 1(2):91-99.
Sun, Shengkun et al., "Isolation of Mouse Marrow Mesenchymal Progenitors by a Novel and Reliable Method," *Stem Cells*, 2003, 21(5):527-535.

(56) References Cited

OTHER PUBLICATIONS

Tagami, Kozo et al., "Elevation of Serum High-Mobility Group Box 1 Protein During Granulocyte Colony-Stimulating Factor-Induced Peripheral Blood Stem Cell Mobilisation," *British Journal of Haematology*, Oct. 10, 2006, 135(4):567-569.
Tagliafico, Enrico et al., "TGFβ/BMP Activate the Smooth Muscle/Bone Differentiation Programs in Mesoangioblasts," *Journal of Cell Science*, 2004, 117(Pt 19):4377-88.
Takahashi, Kunihiko et al., "Effects of HMGB1 on PostInfarction Chronic Heart Failure—Novel Mechanism Regarding Therapeutic Effects of Cell Therapy," *Supplement*, 2011, 27 I-E-19:S189.
Takami, Yoichiro et al., "Synergistic Induction of Hepatocyte Growth Factor in Human Skin Fibroblasts by the Inflammatory Cytokines Interleukin-1 and Interferon-γ," *Biochemical and Biophysical Research Communications*, 2005, 327(1):212-217.
Takeishi, Yasuchika et al., "Importance of Inflammation and Immune Response in Heart Failure—Toll-Like Receptor-Mediated Signaling Pathway and Ventricular Remodeling After Myocardial Infarction," *Journal of Clinical and Experimental Medicine*, Jan. 30, 2010, 232(5):378-385.
Tamai, Katsuto et al., "Development and Outlook of Internal Regeneration-Inducing Pharmaceuticals That Use in vivo Bone Marrow Mesenchymal Stem / Progenitor Cell-Mobilizing Factors," *Gene & Medicine MOOK*, Jul. 22, 2012, 7(22):207-212.
Tamai, Katsuto et al., "New Wave of Wound Healing," *Japanese Journal of Dermatology*, Mar. 2008, 118(4):645, #EL28-4.
Tamai, Katsuto et al., "PDGFRα-positive Cells in Bone Marrow are Mobilized by High Mobility Group Box 1 (HMGB1) to Regenerate Injured Epithelia," http://www.pnas.org/content/suppl/2011/03/31/1016753108.DCSupplemental/pnas.201016753SI.pdf, *PNAS*, Apr. 19, 2011, 108(16):6609-6614.
Tatsumi, Ryuichi et al., "HGF/SF Is Present in Normal Adult Skeletal Muscle and Is Capable of Activating Satellite Cells," *Developmental Biology*, 1998, 194:114-128.
Telusma, Gloria et al., "Dendritic Cell Activating Peptides Induce Distinct Cytokine Profiles," *International Immunology*, Nov. 2006, 18(11):1563-1573.
Thorey, Irmgard S. et al., "The $Ca^{2+}$-Binding Proteins S100A8 and S100A9 Are Encoded by Novel Injury-regulated Genes," *The Journal of Biological Chemistry*, Sep. 21, 2001, 276(38):35818-35825.
Türker, Selcan et al., "Nasal Route and Drug Delivery Systems," *Pharmacy World and Science*, 2004, 26:137-142.
Uchida et al., "The Chemotactic Activity of PDGF-bb, BMP-2, and FGF-2 Towards Committed and Uncommitted Mesenchymal Stem Cells," *The Journal of Japanese Orthopaedic Surgical Society*, 2005, 79(8):S832, 1-P6-6.
Ulloa, Luis et al., "High-mobility group box 1 (HMGB1) protein: Friend and foe," *Cytokine & Growth Factor Reviews*, 2006, 17:189-201.
Vandal, Karen et al., "Blockade of S100A8 and S100A9 Suppresses Neutrophil Migration in Response to Lipopolysaccharide[1]," *The Journal of Immunology*, Sep. 1, 2003, 171(5):2602-2609.
Venereau, Emilie et al., "Mutually exclusive redox forms of HMGB1 promote cell recruitment of proinflammatory cytokine release," *J. Exp. Med.*, 2012, 209(9):1519-1528.
Wang, Huan Liang et al., "High Mobility Group Protein B1 and the Research Progress of its Biological Effect," *Journal of Chinese Modem Surgery*, Dec. 31, 2006, 3(22):1806-1809.
Wang, Huating et al., "Theories and Technologies for Stem Cells," *Series of the 21st Century Biotechnologies*, 2005, pp. 58-61.
Wexler, Sarah A. et al., "Adult Bone Marrow is a Rich Source of Human Mesenchymal 'Stem' Cells but Umbilical Cord and Mobilized Adult Blood Are Not," *British Journal of Haematology*, 2003, 121(2):368-374.
Youn, Ju Ho et al., "High Mobility Group Box 1 Protein Binding to Lipopolysaccharide Facilitates Transfer of Lipopolysaccharide to CD14 and Enhances Lipopolysaccharide-Mediated TNF-α Production in Human Monocytes[1]," *Journal of Immunology*, 2008, 180(7):5067-74.
Yuan, Yan et al., "Differentiation of Mesenchymal Stem Cells in Cardiomyogenic Cells Under the Induction of Myocardial Cell Lysate," *Chinese Journal of Cardiology*, Feb. 2005, 33(2):170-173.
Bianchi, Marco E. et al., "The DNA binding site of HMG1 protein is composed of two similar segments (HMG boxes), both of which have counterparts in other eukaryotic regulatory proteins," *The EMBO Journal*, Mar. 1992, 11(3):1055-1063.
Gong, Wei et al., "The Anti-Inflammatory Activity of HMGB1 A Box is Enhanced When Fused with C-Terminal Acidic Tail," *Journal of Biomedicine and Biotechnology*, vol. 2010, Article ID 915234, 6 pages, 2-10. Doi:10.1155/2010/915234.
Woodbury, Dale et al., "Adult Rat and Human Bone Marrow Stromal Cells Differentiate Into Neurons," *Journal of Neuroscience Research*, Aug. 15, 2000; 61(4):364-370.
Li, Zihai et al., "Heat-Shock Proteins," *Current Protocols in Immunology*, 2003, Supplement 58, A.IT.1-A.IT.6.
Martin-Murphy, Brittany V. et al., "The Role of Damage Associated Molecular Pattern Molecules in Acetaminophen-Induced Liver Injury in Mice," *Toxicol Lett*, Feb. 2010, 192(3):1-20.
Panepucci, Rodrigo A. et al., "Abstract# 4427: Comparison of Gene Expression of Mesenchymal Stem Cells from the Umbilical Cord and from the Bone Marrow," *Blood*, Nov. 2003, 16(102):Abstract.
Pankov, Roumen et al., "Fibronectin at a glance," *J Cell Sci*, Oct. 2002, 115(20):3861-3863.
Santamaria-Kiseil, Liliana et al., "Calcium-dependent and —independent interactions of the S100 protein family," *Biochem J.*, 2006, 396:201-214.
Seong, Yong Seong et al., "Hydrophobicity: an ancient damage-associated molecular pattern that initiates innate immune responses," *Nature Reviews: Immunology*, Jun. 2004, 4(6):469-78.
Soo, Eliza T. L. et al., "Heat Shock Proteins as Novel Therapeutic Targets in Cancer," in vivo, 2008, 22(3):311-5.
Wang, Lei et al., "Ischemic cerebral tissue and MCP-1 enhance rat bone marrow stromal cell migration in interface culture," *Experimental Hematology*, 2002, 30:831-836.
Yamada, Takayuki et al., "Regulation of osteoclast development by Notch signaling directed to osteoclast precursors and through stromal cells," *Blood*, Mar. 2003, 101(6):2227-2234.
Basso, D. Michelle et al., "Basso Mouse Scale for Locomotion Detects Differences in Recovery after Spinal Cord Injury in Five Common Mouse Strains," *Journal of Neurotrauma*, 2006, 23(5):635-659.
Bustin, Michael. "Regulation of DNA-Dependent Activities by the Functional Motifs of the High-Mobility-Group Chromosomal Proteins," *Molecular and Cellular Biology*, Aug. 1999, 19(8):5237-5246.
Fang, Ping et al., "HMGB1 Contributes to Regeneration After Spinal Cord Injury in Adult Zebrafish," *Mol Neurobiol*, 2014, 49:472-483.
Germani, Antonia et al., "Pivotal Advance: High-mobility group box 1 protein—a cytokine with a role in cardiac repair," *Journal of Leukocyte Biology*, Jan. 2007, 81:41-45.
Hori, Osamu et al., "The Receptor for Advanced Glycation End Products (RAGE) Is a Cellular Binding Site for Amphoterin: Mediation of Neurite Outgrowth and Co-Expression of RAGE and Amphoterin in the Developing Nervous System," *The Journal of Biological Chemistry*, Oct. 1995, 270(43):25752-25761.
Merenmies, Jussi et al., "30-kDa Heparin-binding Protein of Brain (Amphoterin) Involved in Neurite Outgrowth," *The Journal of Biological Chemistry*, Sep. 1991, 266(25):16722-16729.
Müller, Susanne et al., "The double life of HMGB1 chromatin protein: architectural factor and extracellular signal," *The EMBO Journal*, 2001, 20(16):4337-4340.
Nakajima et al., "Dynamics and Role of High Mobility Group Box-1 (HMGB-1) in Injured Spinal Cord," *Nihon Seikei Geka Gakkai Zasshi (J. Jpn. Orthop. Assoc.)*, 2010, 84(8):S1050.
Palumbo, Roberta et al., "Extracellular HMBG1, a signal of tissue damage, induces mesoangioblast migration and proliferation," *The Journal of Cell Biology*, Feb. 2004, 164(3):441-449.
Quertainmont, Renaud et al., "Mesenchymal Stem Cell Graft Improves Recovery after Spinal Cord Injury in Adult Rats through Neurotrophic and Pro-Angiogenic Actions," *PLoS One*, Jun. 2012, 7(6):1-15.

(56) References Cited

OTHER PUBLICATIONS

Rahimi-Movaghar, Vafa. "Effect of Decompression on Complete Spinal Cord Injury in Rats," *International Journal of Neuroscience*, 2008, 118:1359-1373.

Tamai, Katsuto et al. "PDGFRα-positive cells in bone marrow are mobilized by high mobility group box 1 (HMGB1) to regenerate injured epithelia," *Proceedings of the National Academy of Sciences*, Apr. 19, 2011, 108(16): 6609-6614.

Tamai, Katsuto et al., U.S. Appl. No. 11/997,475, "Mesenchymal Stem Cell Inducer, Tissue Regeneration Promoter and Method of Preparing Mesenchymal Stem Cell," filed on Jan. 31, 2008, in the name of Genomix Co., Ltd.

Wang, Haichao et al., "HMG-1 as a Late Mediator of Endotoxin Lethality in Mice," *Science*, Jul. 1999, 285:248-251.

Wu, Yaojiong et al., "Mesenchymal Stem Cells Enhance Wound Healing Through Differentiation and Angiogenesis," *Stem Cells*, 2007, 25:2648-2659.

Yang, De et al., "High mobility group box-1 protein induces the migration and activation of human dendritic cells and acts as an alarmin," *Journal of Leukocyte Biology*, Jan. 2007, 81:59-66.

Herrera, M.B., et al., "Exogenous mesenchymal stem cells localize to the kidney by means of CD44 following acute tubular injury," *Kidney International*, 2007; 72:430-441.

Jiao, C., et al., "Researchers find nerve damage may precede diabetic retinopathy." *EurekAlert! Science News*, Apr. 2016, https://www.eurekalert.org/pub_releases/2016-04/uoih-rfv042616.php.

Morosetti, R., et al., "MyoD expression restores defective myogenic differentiation of human mesoangioblasts from inclusion-body myositis muscle." *PNAS*, Nov. 7, 2006, 103(45): 16995-17000.

Slater, M., et al., "Endometriotic cells exhibit metaplastic change and oxidative DNA damage as well as decreased function, compared to normal endometrium." *Journal of Molecular Histology*, 2005, 36(4): 257-263.

Tang, Daolin, et al., "High-Mobility Group Box 1, Oxidative Stress, and Disease," *Antioxidants & Redox Signaling*, 2011; 14(7): 1315-1335. DOI: 10.1089/ars.2010.3356.

Wolf, G., et al., "From the Periphery of the Glomerular Capillary Wall Toward the Center of Disease." *Diabetes*, Jun. 2005, 54(6): 1626-1634.

Arminan, Ana et al., "Mesenchymal Stem Cells Provide Better Results Than Hematopoietic Precursors for the Treatment of Myocardial Infarction." *JACC*, May 18, 2010, 55(20): 2244-2253.

Berry, Mark F., et al., "Mesenchymal stem cell injection after myocardial infarction improves myocardial compliance." *Am J Physiol Heart Ciro Physiol*, Jun. 2006, 290(6): H2196-H2203.

Ishikane, Shin, "Therapeutic application of allogenic fetal membrane-derived mesenchymal stem cells transplantation in regenerative medicine." *Pharmaceutical Bulletin of Fukuoka University*, Mar. 2011, 11(0): 17-25.

Li, Ying et al., "Advancement of Human Multiply, Sex health and Reproductive Medical Science." *Peking University Medical Press*, Mar. 2007, $1^{st}$ Edition, 270-271.

Takahashi, Kunihiko, et al., "Modulated Inflammation by Injection of High-Mobility Group Box 1 Recovers Post-Infarction Chronically Failing Heart." *Circulation*, Sep. 2008, 118(14 Suppl): S106-S114.

Wang, Wei et al., "Intravenous administration of bone marrow mesenchymal stromal cells is safe for the lung in a chronic myocardial infarction model." *Regen Med*, Mar. 2011, 6(2): 179-190.

Wang, Yaping, "Biology of hematopoietic stem cell and the research method thereof." *Science Press*, Mar. 2007, 1st Edition, 56-58.

Bianchi, Me, "High mobility group 1 protein (HMGB1) N-terminal peptide." pp. 1 (sequence listing) May 27, 2004 [online] [retrieved on Jul. 26, 2016]. Retrieved from: EPOQUE Database.

Hmgbiotech SRL, "BoxA from HMGB1, human & mouse LPS-free." [online]., pp. 1-2, 2008-2017 [retrieved on Jan. 27, 2017]. Retrieved from the Internet: <URL: http://www.hmgbiotech.com/products.php?ID=91>.

Hmgbiotech SRL, "BoxA from HMGB1, human & mouse LPS-free. Datasheet" [online]. pp. 1, 2008 [retrieved on Jan. 31, 2017]. Retrieved from the Internet: <URL:http://www.hmgbiotech.com/upload/documenti/0515122144_boxa>.

University of Michigan Health System, "Age-related Macular Degeneration," pp. 1-3, Aug. 21, 2015, http://www.uofmhealth.org/health-library/hw176038.

* cited by examiner

Normal Group

×5

×10

PBS Group

Peptide 11-44

SEQUENCE LISTING

```
<160> NUMBER OF SEQ ID NOS: 5

<210> SEQ ID NO 1
<211> LENGTH: 215
<212> TYPE: PRT
<213> ORGANISM: Homo sapiens

<400> SEQUENCE: 1

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175
```

```
Lys Ala Glu Lys Ser Lys Lys Lys Glu Glu Glu Glu Asp Glu
            180                 185                 190

Asp Glu Glu Asp Glu Glu Glu Glu Asp Glu Asp Glu Asp Glu
        195                 200                 205

Glu Glu Asp Asp Asp Asp Glu
    210                 215

<210> SEQ ID NO 2
<211> LENGTH: 648
<212> TYPE: DNA
<213> ORGANISM: Homo sapiens

<400> SEQUENCE: 2
atgggcaaag gagatcctaa gaagccgaga ggcaaaatgt catcatatgc attttttgtg      60
caaacttgtc gggaggagca taagaagaag cacccagatg cttcagtcaa cttctcagag     120
ttttctaaga agtgctcaga gaggtggaag accatgtctg ctaaagagaa aggaaaattt     180
gaagatatgg caaagcggaa caaggcccgt tatgaaagag aaatgaaaac ctatatccct     240
cccaaagggg agacaaaaaa gaagttcaag gatcccaatg cacccaagag gcctccttcg     300
gccttcttcc tcttctgctc tgagtatcgc ccaaaaatca aggagaacaa tcctggcctg     360
tccattggtg atgttgcgaa gaaactggga gagatgtgga ataacactgc tgcagatgac     420
aagcagccct tatgaaaagaa ggctgcgaag ctgaaggaaa aatacgaaaa ggatattgct     480
gcatatcgag ctaaaggaaa gcctgatgca gcaaaaaagg gagttgtcaa ggctgaaaaa     540
agcaagaaaa agaaggaaga ggaggaagat gaggaagatg aagaggatga ggaggaggag     600
gaagatgaag aagatgaaga tgaagaagaa gatgatgatg atgaataa                  648

<210> SEQ ID NO 3
<211> LENGTH: 9
<212> TYPE: PRT
<213> ORGANISM: Artificial sequence
<220> FEATURE:
<223> OTHER INFORMATION: Synthesized peptide from the HMGB1 protein

<400> SEQUENCE: 3

Ala Phe Phe Val Gln Thr Cys Arg Glu
1               5

<210> SEQ ID NO 4
<211> LENGTH: 34
<212> TYPE: PRT
<213> ORGANISM: Artificial sequence
<220> FEATURE:
<223> OTHER INFORMATION: Synthesized peptide from the HMGB1 protein

<400> SEQUENCE: 4

Gly Lys Met Ser Ser Tyr Ala Phe Phe Val Gln Thr Cys Arg Glu Glu
1               5                   10                  15

His Lys Lys Lys His Pro Asp Ala Ser Val Asn Phe Ser Glu Phe Ser
            20                  25                  30

Lys Lys

<210> SEQ ID NO 5
<211> LENGTH: 44
<212> TYPE: PRT
<213> ORGANISM: Artificial sequence
<220> FEATURE:
<223> OTHER INFORMATION: Synthesized peptide from the HMGB1 protein
```

```
<400> SEQUENCE: 5

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys
                35                  40
```

METHOD FOR TREATING SPINAL CORD INJURY USING HMGB1 FRAGMENT

CROSS REFERENCE TO A RELATED APPLICATION

This application is a National Stage Application of International Application Number PCT/JP2013/078759, filed Oct. 24, 2013; which claims priority to Japanese Patent Application No. 2012-235786, filed Oct. 25, 2012; both of which are incorporated herein by reference in their entirety.

The Sequence Listing for this application is labeled "SeqList-17Apr15.txt", which was created on Apr. 17, 2015, and is 5 KB. The entire content is incorporated herein by reference in its entirety

TECHNICAL FIELD

The present invention relates to novel therapeutic pharmaceutical compositions for injury of the spinal cord which comprise an HMGB1 fragment, and uses thereof.

BACKGROUND ART

Bone marrow mesenchymal stem cells are pluripotent in vivo stem cells, and they are known to differentiate into osteoblasts, adipocytes, cartilage and such. Recently, it is beginning to be reported that in patients with tissue damage such as cerebral infarction, administration of their own bone marrow mesenchymal stem cells can promote healing of the tissue damage. However, since bone marrow mesenchymal stem cells are scarce cells in the bone marrow, there is a limit to the amount that can be collected from a patient. Therefore, obtaining the amount of bone marrow mesenchymal stem cells necessary for treatment of a wide range of tissue damages is difficult. At present, the method of culturing the bone marrow mesenchymal stem cells for proliferation to secure the number of cells needed for treatment is adopted. However, it is very difficult to culture bone marrow mesenchymal stem cells while maintaining their undifferentiated state. Furthermore, there are many associated problems to be solved, such as viral and bacterial contamination and canceration of cells. Furthermore, the cost for culturing cells that are guaranteed with safety and quality is huge.

On the other hand, bone marrow mesenchymal stem cells have been known to have an effect of facilitating the healing of spinal cord injury as well. This is assumed to arise from differentiation of pluripotent bone marrow mesenchymal stem cells into nerve cells, and supply of components having an effect of improving tissue damage such as growth factors by bone marrow mesenchymal stem cells accumulated at the damaged tissues.

PRIOR ART DOCUMENTS

Patent Documents

[Patent Document 1] WO2008/053892
[Patent Document 2] WO2007/015546
[Patent Document 3] WO2009/133939
[Patent Document 4] WO2009/133943
[Patent Document 5] WO2009/133940
[Patent Document 6] WO2004/004763

Non-Patent Documents

[Non-patent Document 1] Bustin et al., Mol Cell Biol, 19: 5237-5246, 1999
[Non-patent Document 2] Hori et al., J. Biol. Chem., 270, 25752-25761, 1995
[Non-patent Document 3] Wang et al., Science, 285: 248-251, 1999
[Non-patent Document 4] Muller et al., EMBO J, 20: 4337-4340, 2001
[Non-patent Document 5] Wang et al., Science, 285: 248-251, 1999
[Non-patent Document 6] Germani et al., J Leukoc Biol., 81(1): 41-5, 2007
[Non-patent Document 7] Palumbo et al., J. Cell Biol., 164: 441-449, 2004
[Non-patent Document 8] Merenmies et al., J. Biol. Chem., 266: 16722-16729, 1991
[Non-patent Document 9] Wu Y et al., Stem cells, 25: 2648-2659, 2007
[Non-patent Document 10] Tamai et al., Proc Natl Acad Sci USA., 108(16): 6609-6614, 2011
[Non-patent Document 11] Yang et al., J Leukoc Biol., 81(1): 59-66, 2007
[Non-patent Document 12] Basso et al., J Neurotrauma., 23(5): 635-659, 2006
[Non-patent Document 13] Rahimi-Movaghar et al., Int J Neurosci., 118(10): 1359-1373, 2008
[Non-patent Document 14] Quertainmont R et al., PloS One., 7(6):e39500, 2012

SUMMARY OF THE INVENTION

Problems to be Solved by the Invention

Spinal cord injury is a disease where patients experience extreme loss of quality of life such as difficulty in walking due to paralysis of the lower half of the body. However, spontaneous recovery cannot be expected and effective treatment methods have not been established. As described above, currently, there are expectations in applying regenerative medicine such as cell therapy to treatment of spinal cord injury, but it is still in the process of development. Furthermore, even if it is put to practical use, the problem of large medical expense has not yet been solved.

However, if healing of spinal cord injury can be promoted by administering a pharmaceutical having an activity of mobilizing bone marrow mesenchymal stem cells to the damaged site, it is expected that inexpensive and safe therapeutic methods can be provided to patients with spinal cord injury for which effective methods of treatment hardly exist at present.

Means for Solving the Problems

So far, the present inventors have revealed that High Mobility Group Box 1 (HMGB1) is a protein that has an activity of stimulating the migration of mesenchymal stem cells in the bone marrow and mobilizing the cells into blood. HMGB1 is primarily known to be a major component of a non-histone nuclear protein, and has two DNA-binding domains, Box A and Box B, in the molecule. Furthermore, a known function of HMGB1 in the nucleus is to relax the nucleosome structure and to form a structure optimal for transcription reaction. However, in recent years, it has become clear that the nuclear protein HMGB1 is secreted to the outside of cells to exert various activities, even though it does not have a secretion signal. Research on its function as a mediator of inflammation is most advanced. For example, in a mouse sepsis model (LPS administration model), HMGB1 secreted from macrophages due to TNFα stimulation was found to be a mediator of sepsis (Wang et al.: Science 1999; 285: 248-251), and TLR4 is known to be a candidate receptor. Furthermore, the most well-known HMGB1 receptor is RAGE, and binding between this receptor and HMGB1 has been reported to influence migration activity of cells and inflammatory signal transduction.

The present invention discloses novel therapeutic pharmaceutical compositions for injury of the spinal cord which comprises an HMGB1 fragment, and uses thereof.

Specifically, the present inventors produced a peptide consisting of the amino acids at positions 1 to 44 of the HMGB1 protein (SEQ ID NO: 5), and an HMGB1 fragment consisting of the amino acids at positions 11 to 44 (SEQ ID NO: 4) by peptide synthesis. Each of the produced HMGB1 fragments was administered to disease model mice that enable evaluation of therapeutic effects on injury of the spinal cord, and therapeutic effects of the fragments on injury of the spinal cord were confirmed.

Based on these findings, the present application provides the following invention:

[1] a pharmaceutical composition for use in the treatment of injury of the spinal cord, which comprises a HMGB1 fragment peptide;
[2] the pharmaceutical composition of [1], wherein the HMGB1 fragment peptide is a peptide comprising an amino acid sequence selected from the group consisting of SEQ ID NO: 3, SEQ ID NO: 4, and SEQ ID NO: 5;
[3] the pharmaceutical composition of [1], wherein the HMGB1 fragment peptide is a peptide consisting of an amino acid sequence selected from the group consisting of SEQ ID NO: 3, SEQ ID NO: 4, and SEQ ID NO: 5;
[4] a method for treating injury of the spinal cord, comprising the step of administering an HMGB1 fragment peptide;
[5] the method of [4], wherein the HMGB1 fragment peptide is a peptide comprising the amino acid sequence selected from the group consisting of SEQ ID NO: 3, SEQ ID NO: 4, and SEQ ID NO: 5;
[6] the method of [4], wherein the HMGB1 fragment peptide is a peptide consisting of the amino acid sequence selected from the group consisting of SEQ ID NO: 3, SEQ ID NO: 4, and SEQ ID NO: 5;
[7] an HMGB1 fragment peptide for use in the treatment of injury of the spinal cord;
[8] the HMGB1 fragment peptide of [7], wherein the HMGB1 fragment peptide is a peptide comprising the amino acid sequence selected from the group consisting of SEQ ID NO: 3, SEQ ID NO: 4, and SEQ ID NO: 5;
[9] the HMGB1 fragment peptide of [7], wherein the HMGB1 fragment peptide is a peptide consisting of the amino acid sequence selected from the group consisting of SEQ ID NO: 3, SEQ ID NO: 4, and SEQ ID NO: 5;
[10] use for the production of a medicament for use in the treatment of injury of the spinal cord, comprising an HMGB1 fragment peptide;
[11] the use of [10], wherein the HMGB1 fragment peptide is a peptide comprising the amino acid sequence selected from the group consisting of SEQ ID NO: 3, SEQ ID NO: 4, and SEQ ID NO: 5; and
[12] the use of [10], wherein the HMGB1 fragment peptide is a peptide consisting of the amino acid sequence selected from the group consisting of SEQ ID NO: 3, SEQ ID NO: 4, and SEQ ID NO: 5.

BRIEF DESCRIPTION OF THE DRAWINGS

FIG. 2B shows HE staining of the spinal cord. The size of the area of injury of the spinal cord decreased in the HMGB1 fragment (11-44)-administered group as compared to that of the negative control (PBS-administered) group, and therapeutic effects were also observed in the pathological tissues.

MODE FOR CARRYING OUT THE INVENTION

The present invention provides pharmaceutical compositions for use in the treatment of injury of the spinal cord, which comprises an HMGB1 fragment peptide having cell migration-stimulating activity. Herein, pharmaceutical compositions for use in the treatment of injury of the spinal cord of the present invention are also expressed as medicaments, pharmaceutical agents, or medicinal compositions.

In the present invention, "injury of the spinal cord" means extrinsic or intrinsic injury of the spinal cord. Extrinsic injury of the spinal cord includes, for example, traumatic injury of the spinal cord, but is not limited thereto. Herein, extrinsic injury of the spinal cord may be expressed simply as "spinal cord injury".

In the present invention, a cell migration-stimulating activity refers to the activity of stimulating cell migration. Herein, a cell migration-stimulating activity is also expressed as a cell migration-inducing activity or a cell-attracting activity.

The pharmaceutical compositions of the present invention can be administered/added to any sites. That is, the compositions can exert their effects no matter at which site they are administered, such as a site of injury of the spinal cord in need of regeneration, a site other than the lesion site, or blood. For example, when the compositions are administered/added, cells are recruited to the site of administration/addition or its nearby sites, thereby inducing or promoting regeneration of the lesion. Also, for example, when the compositions are administered/added to a lesion site or to the vicinity thereof, cells are recruited to the lesion, thereby inducing or promoting regeneration of the lesion. Further, for example, when the compositions are administered/added to a tissue other than a tissue in need of regeneration, bone marrow cells are mobilized from bone marrow to the tissue in need of regeneration through peripheral circulation, thereby inducing or promoting tissue regeneration. Here, "peripheral circulation" is also called "blood circulation" or "peripheral circulation bloodstream".

Administration to a tissue other than a tissue in need of regeneration refers to administration to a site that is not a site in need of regeneration (a site other than a site in need of regeneration). Accordingly, "a tissue other than a tissue in need of regeneration" can also be referred to as:
a site other than a tissue in need of regeneration; a site other than a site in need of regeneration; a site distant from a tissue in need of regeneration; a site distant from a site in need of regeneration; a site distal to a site in need of regeneration; a tissue distal to a tissue in need of regeneration; a distal site; or a distal tissue.
Thus, compositions of the present invention are effectively used to regenerate tissues to which it is difficult to directly administer pharmaceutical agents from outside of the body. Examples of the tissue other than a tissue in need of regeneration include blood tissues, muscle tissues, subcutaneous tissues, intradermal tissues, abdominal cavity, and such.

In the present invention, cells that are stimulated to migrate or cells mobilized from bone marrow to peripheral blood include undifferentiated cells and cells in various stages of differentiation, but are not limited thereto. In the present invention, cells that are stimulated to migrate or cells mobilized from bone marrow to peripheral blood include stem cells, non-stem cells, and such, but are not limited thereto. Stem cells include circulatory stem cells and non-circulatory stem cells. Non-circulatory stem cells are, for example, stem cells residing in a tissue. Circulatory stem cells are, for example, circulatory stem cells in blood.

Further, cells stimulated to migrate or cells mobilized from bone marrow to peripheral blood include bone marrow-derived cells and hematopoietic stem cells, but are not limited thereto. In the present specification, "hematopoietic stem cells" are stem cells that can differentiate into blood cells such as red blood cells, platelets, mast cells, and dendritic cells, as well as white blood cells including neutrophils, eosinophils, basophils, lymphocytes, monocytes, macrophages, and such. Their markers are known to be CD34-positive and CD133-positive in human, and CD34-negative, c-Kit-positive, Sca-1-positive, and lineage marker-negative in mouse. Hematopoietic stem cells are difficult to be cultured alone when cultured in culture dishes, and they need to be co-cultured with stromal cells.

In the present specification, "bone marrow cells" means cells present inside bone marrow while "bone marrow-derived cells" means "bone marrow cells" mobilized from bone marrow to outside of bone marrow. "Bone marrow cells" include cells containing tissue progenitor cell populations present inside bone marrow. Further, "bone marrow-derived cells" may be cells containing mesoangioblasts or cells free of mesoangioblasts.

Tissue progenitor cells are defined as undifferentiated cells having a unidirectional potency to differentiate into cells of a specific tissue other than the blood system, and include undifferentiated cells having the potency to differentiate into mesenchymal tissues, epithelial tissues, nerve tissues, parenchymatous organs, and vascular endothelium as mentioned above.

Herein, "bone marrow mesenchymal stem cells", "bone marrow stromal pluripotent cells" or "bone marrow pluripotent stem cells" refer to cells existing in the bone marrow, which are directly collected from the bone marrow or indirectly collected from other tissues (blood, skin, fat, and other tissues), and can be cultured and proliferated as adherent cells on a culture dish (made of plastic or glass). These cells are characterized in having a potential to differentiate into mesenchymal tissues such as bone, cartilage, and fat (mesenchymal stem cells), or into skeletal muscle, heart muscle, nervous tissues, and epithelial tissues (pluripotent stem cells), and can be obtained by collection of bone marrow cells.

"Bone marrow cells" and "bone marrow-derived cells" are hematopoietic stem cells and differentiated cells derived therefrom such as leukocytes, erythrocytes, platelets, osteoblasts, and fibrocytes, or are stem cells represented by cells which have been hitherto called bone marrow mesenchymal stem cells, bone marrow stromal pluripotent stem cells, or bone marrow pluripotent stem cells. As used herein, "bone marrow stem cells" refer to stem cells present inside bone marrow, while "bone marrow-derived stem cells" refer to "bone marrow stem cells" mobilized from bone marrow to outside of bone marrow. In the present invention, cells stimulated to migrate or cells mobilized from bone marrow to peripheral blood include "bone marrow-derived stem cells", but are not limited thereto. "Bone marrow cells" and "bone marrow-derived cells" can be isolated by bone marrow collection (bone marrow cell collection) or peripheral blood collection. Hematopoietic stem cells are nonadherent, while some of the "bone marrow cells" and "bone marrow-derived cells" are obtained as adherent cells by means of a cell culture of a monocyte fraction of blood obtained by the bone marrow collection (bone marrow cell collection) or peripheral blood collection.

Moreover, "bone marrow cells" and "bone marrow-derived cells" include mesenchymal stem cells, and have a potential to differentiate into, preferably, osteoblasts (which can be identified by observing calcification after inducing differentiation), chondrocytes (which can be identified by alcian blue positive staining, safranin O positive staining, or the like), adipocytes (which can be identified by Sudan III positive staining), and other mesenchymal cells such as fibroblasts, smooth muscle cells, stromal cells, and tendon cells; and further nerve cells, epithelial cells (for example, epidermal keratinocytes and intestinal epithelial cells express cytokeratin family), and vascular endothelial cells. The cells to be differentiated into are not limited to the above cells, and the potential to differentiate into cells of parenchymatous organs such as liver, kidney, and pancreas is also included.

On the other hand, "bone marrow-derived bone marrow mesenchymal stem cells", "bone marrow-derived bone marrow stromal pluripotent cells", or "bone marrow-derived bone marrow pluripotent stem cells" mobilized from bone marrow to outside of the bone marrow are cells that can be obtained by collection from peripheral blood, mesenchymal tissues such as fat, epithelial tissues such as skin, or nervous tissues such as brain.

In addition, these cells are also characterized in having a potential to differentiate into, for example, epithelial tissues such as keratinocytes that constitute skin, or nervous tissues that constitute brain, when administered to a lesion area of the living body immediately after collection or after once being adhered onto a culture dish.

Bone marrow mesenchymal stem cells, bone marrow stromal pluripotent stem cells, bone marrow pluripotent stem cells, or these cells recruited from bone marrow to outside of the bone marrow preferably have a potency to differentiate into: osteoblasts (which can be identified by observing calcification after inducing differentiation), chondrocytes (which can be identified by alcian blue positive staining, safranin O positive staining, or the like), adipocytes (which can be identified by Sudan III positive staining or the like), and other mesenchymal cells such as fibroblasts, smooth muscle cells, skeletal muscle cells, stromal cells, and tendon cells; nerve cells, pigment cells, epidermal cells, hair follicle cells (which express cytokeratin family, hair keratin family, or the like), epithelial cells (for example, epidermal keratinocytes and intestinal epithelial cells express cytokeratin family or the like), and endothelial cells; and further into cells of parenchymatous organs such as liver, kidney, and pancreas. However, differentiated cells are not limited to the above cells.

Human bone marrow cells and human bone marrow-derived cells can be exemplified by, but are not limited to, cells which can be directly obtained by collecting bone marrow (bone marrow cells), peripheral blood, or fat, or obtained as adherent cells through culturing of an isolated monocyte fraction. Markers for human bone marrow cells and human bone marrow-derived cells include, for example, all or some of the following but are not limited thereto: PDGFRα-positive, Lin-negative, CD45-negative, CD44-positive, CD90-positive, and CD29-positive, Flk-1-negative, CD105-positive, CD73-positive, CD90-positive, CD71-positive, Stro-1-positive, CD106-positive, CD166-positive, and CD31-negative.

Moreover, mouse bone marrow cells and mouse bone marrow-derived cells can be exemplified by, but are not limited to, cells which can be directly obtained by collecting bone marrow (bone marrow cells), peripheral blood, or fat, or obtained as adherent cells through culturing of an isolated monocyte fraction. Markers for mouse bone marrow cells and mouse bone marrow-derived cells include, for example, all or some of the following but are not limited thereto: CD44-positive, PDGFRα-positive, PDGFRβ-positive, CD45-negative, Lin-negative, Sca-1 positive, c-kit negative, CD90-positive, CD29-positive, and Flk-1-negative.

In the present invention, cells stimulated to migrate include PDGFRα-positive cells, but are not limited thereto. In addition, PDGFRα-positive cells stimulated to migrate are not particularly limited, but preferably are bone marrow-derived PDGFRα-positive cells. Further, markers other than PDGFRα can be exemplified by all or some of CD29-positive, CD44-positive, CD90-positive, CD271-positive, CD11b-negative, and Flk-1-negative, but are not limited thereto. PDGFRα-positive cells include, but are not limited to, for example, PDGFRα-positive bone marrow-derived cells, PDGFRα-positive bone marrow-derived mesenchymal stem cells, tissue cells residing in PDGFRα-positive tissues (for example, fibroblasts and such), PDGFRα-positive bone marrow-derived cells obtained as adherent cells by means of cell culture of a monocyte fraction of blood obtained by bone marrow collection (bone marrow cell collection) or peripheral blood collection.

The HMGB1 protein in the present invention includes, but is not limited to, for example, a protein comprising the amino acid sequence of SEQ ID NO: 1 as a human-derived HMGB1 protein, and DNA encoding said protein includes, but is not limited to, for example, a DNA comprising the nucleotide sequence of SEQ ID NO: 2.

In the present invention, "an HMGB1 fragment peptide having a cell migration-stimulating activity" refers to a peptide consisting of a portion of an HMGB1 protein and having a cell migration-stimulating activity. Fragment peptides consisting of a portion of the HMGB1 protein of the present invention are not particularly limited as long as they have a cell migration-stimulating activity, but are preferably an HMGB1 fragment peptide that comprises at least the amino acid sequence of positions 17 to 25 of the HMGB1 protein (SEQ ID NO: 3), which is confirmed by experiments performed by the present inventors to be the smallest peptide fragment among the fragments with cell migration-stimulating activity (FIG. 1).

In the present invention, peptides consisting of an HMGB1 fragment that has cell migration-stimulating activity are, for example, the fragments below, but are not limited thereto.

In the present invention, HMGB1 fragments which have a cell migration-stimulating activity include a fragment peptide comprising an amino acid sequence selected from the group consisting of the amino acid sequences of SEQ ID NO: 3, SEQ ID NO: 4, and SEQ ID NO: 5, which is an HMGB1 fragment peptide having cell migration-stimulating activity. These fragment peptides include, for example, a fragment peptide comprising at least the fragment peptide (17-25) of SEQ ID NO: 3 with the upper limit being the fragment peptide (11-44) of SEQ ID NO: 4; a fragment peptide comprising at least the fragment peptide (11-44) of SEQ ID NO: 4 with the upper limit being the fragment peptide (1-44) of SEQ ID NO: 5; or a fragment peptide comprising at least the fragment peptide (17-25) of SEQ ID NO: 3 with the upper limit being the fragment peptide (1-44) of SEQ ID NO: 5; but are not limited thereto.

In the present invention, HMGB1 fragment peptides which have a cell migration-stimulating activity include, for example, a fragment peptide consisting of an amino acid sequence selected from the group consisting of the amino acid sequences of SEQ ID NO: 3, SEQ ID NO: 4, and SEQ ID NO: 5, which is an HMGB1 fragment peptide having cell migration-stimulating activity.

Methods for administering a composition of the present invention include oral administration and parenteral administration. Specifically, parenteral administration includes, but is not limited to, injection, transnasal administration, transpulmonary administration, transdermal administration, and such. As examples of injection, intravenous injection, intramuscular injection, intraperitoneal injection, subcutaneous injection, and such can be used to administer a composition of the present invention systemically or locally (for example, under the skin, in the skin, on the surface of skin, eyeball or palpebral conjunctiva, nasal cavity mucosa, intraoral mucosa and mucosa of the gastrointestinal tract, vaginal mucosa/intrauterine mucosa, damage site or such).

Methods of administering a composition of the present invention include, but are not limited to, for example, intravascular administration (intra-arterial administration, intravenous administration, or such), blood administration, intramuscular administration, subcutaneous administration, intradermal administration, intraperitoneal administration.

There is no limitation on the site of administration, and for example, it may be a tissue site in need of regeneration or its nearby region, a site different from the tissue in need of regeneration, or a site distant to and different from the tissue in need of regeneration. The site is, for example, in the blood (in arteries, in veins, or such), muscle, under the skin, in the skin, in the abdominal cavity, or such, without being limited thereto.

The method of administration may be appropriately selected according to the age and the symptoms of the patient. When a peptide of the present invention is administered, the dose per time of the peptide can be selected within a range of 0.0000001 mg to 1000 mg per kg body weight of a patient. Alternatively, the dose can be selected within a range of 0.00001 mg to 100000 mg per body of patient, for example. When administering cells secreting a peptide of the present invention or gene therapy vectors inserted with DNA encoding the peptide, they may be administered such that the amount of the peptide is within the above range. However, the dose of pharmaceutical compositions of the present invention is not limited thereto.

HMGB1 peptide fragments of the present invention can be obtained as recombinants by incorporating a DNA encoding the peptide into an appropriate expression system, or can be synthesized artificially. Pharmaceutical compositions of the present invention can be formulated according to the usual methods (for example, Remington's Pharmaceutical Science, latest edition, Mark Publishing Company, Easton, U.S.A), and may contain pharmaceutically acceptable carriers and additives together. Examples include surfactants, excipients, colorants, perfumes, preservatives, stabilizers, buffers, suspending agents, isotonizing agents, binders, disintegrants, lubricants, flow promoters, and flavoring agents, although they are not limited thereto and other common carriers may be appropriately used. Specific examples include light anhydrous silicic acid, lactose, crystalline cellulose, mannitol, starch, carmellose calcium, carmellose sodium, hydroxypropylcellulose, hydroxypropylmethylcellulose, polyvinylacetaldiethylamino acetate, polyvinylpyrrolidone, gelatin, medium-chain fatty acid triglyceride, polyoxyethylene hydrogenated castor oil 60, white sugar, carboxymethyl cellulose, corn starch, and inorganic salts.

All prior art documents cited herein are incorporated herein by reference.

Herein below, the present invention will be further illustrated with reference to Examples, but it is not to be construed as being limited thereto.

Example 1

Assessment of Synthetic Peptides for Migration-Promoting Activity
(Methods)

The peptides listed below were custom synthesized using the solid phase method by Medical & Biological Laboratories (MBL). The peptides were synthesized based on the mouse HMGB1 sequence. Amino acid sequences from positions 1 to 169 of mouse HMGB1 and human HMGB1 are identical, i.e., shares 100% sequence homology.
A synthetic peptide consisting of the amino acid sequence from positions 1 to 10 of HMGB1 (1-10);
a synthetic peptide consisting of the amino acid sequence from positions 1 to 34 of HMGB1 (1-34);
a synthetic peptide consisting of the amino acid sequence from positions 11 to 20 of HMGB1 (11-20);
a synthetic peptide consisting of the amino acid sequence from positions 11 to 25 of HMGB1 (11-25);
a synthetic peptide consisting of the amino acid sequence from positions 11 to 30 of HMGB1 (11-30);
a synthetic peptide consisting of the amino acid sequence from positions 11 to 34 of HMGB1 (11-34);
a synthetic peptide consisting of the amino acid sequence from positions 11 to 44 of HMGB1 (11-44); and
the full-length mouse HMGB1 produced in HEK293 (1-215 (HEK)) as a positive control were adjusted to 100 µg/ml and placed in the lower chamber of a chemotaxis chamber to assess the migration-promoting activity on mouse bone marrow mesenchymal stem cell line (MSC-1 cell; produced by Osaka University, Tamai et al., (Tamai et al., Proc Natl Acad Sci USA., 108(16): 6609-6614, 2011)).
(Results)

Figure 1A:
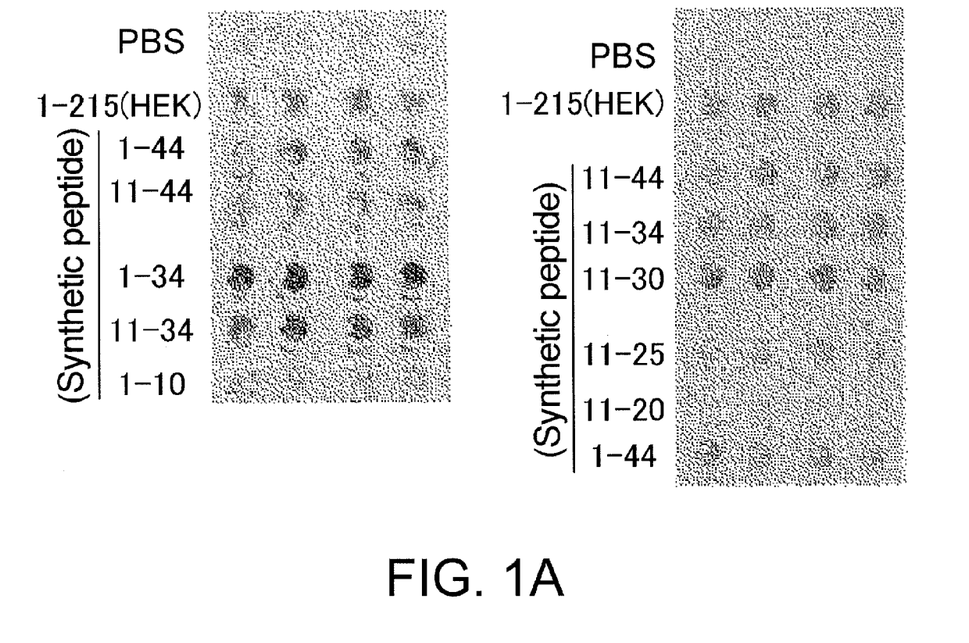
FIG. 1A shows photographs indicating the migration-stimulating activity of various synthetic peptides on established PDGFRα-positive bone marrow mesenchymal stem cells. All fragment peptides containing the smallest fragment, the HMGB1 fragment peptide (17-25), show cell migration-stimulating activity.

At least synthetic peptides (11-34), (1-34), (11-44), (1-44), and (11-30) were found to have the activity comparable to or higher than that of the positive control (FIG. 1A). Furthermore, synthetic peptide (11-25) was also found to have the activity (FIG. 1A).
(Methods)

In order to narrow down the location of the active center, the shorter peptides listed below were synthesized.
a synthetic peptide consisting of the amino acid sequence from positions 11 to 25 of HMGB1 (11-25),
a synthetic peptide consisting of the amino acid sequence from positions 12 to 25 of HMGB1 (12-25),
a synthetic peptide consisting of the amino acid sequence from positions 13 to 25 of HMGB1 (13-25),
a synthetic peptide consisting of the amino acid sequence from positions 14 to 25 of HMGB1 (14-25),
a synthetic peptide consisting of the amino acid sequence from positions 15 to 25 of HMGB1 (15-25),
a synthetic peptide consisting of the amino acid sequence from positions 16 to 25 of HMGB1 (16-25), and
a synthetic peptide consisting of the amino acid sequence from positions 17 to 25 of HMGB1 (17-25).

As positive controls, centrifuged supernatant of the skin of a one-day-old mouse (one individual) incubated in PBS at 4° C. for 12 hours, and the full-length mouse HMGB1 produced in HEK293 (1-215(HEK)) were used. Cells of a bone marrow mesenchymal stem cell line (MSC-1) were placed in the upper chamber of a chemotaxis chamber, and the protein and synthetic peptides were added at a concentration of 5 µM or 10 µM to the lower chamber of the chemotaxis chamber. The migration assay was carried out by the same method as described above.
(Results)

Figure 1B:
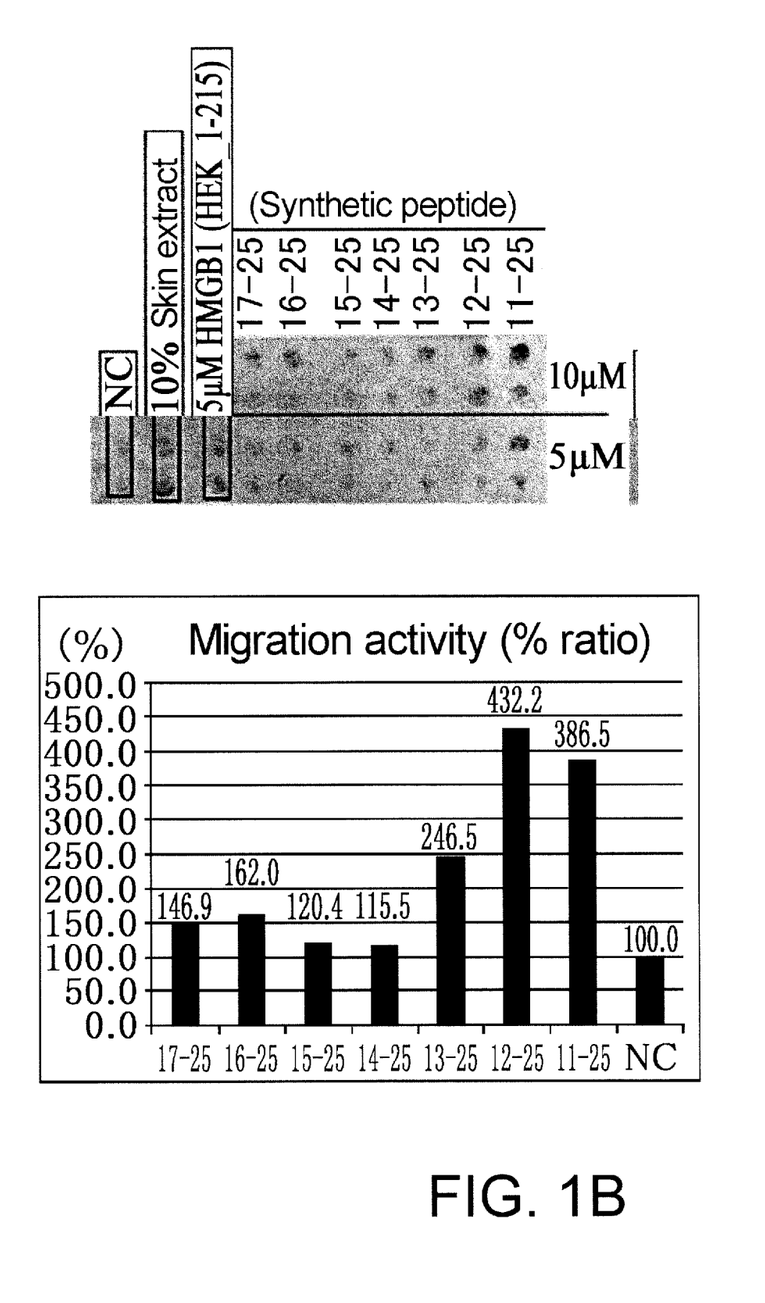
FIG. 1B is a photograph showing the migration-stimulating activity of HMGB1 fragment peptides with different lengths on established PDGFRα-positive bone marrow mesenchymal stem cells. Each peptide was prepared by peptide synthesis. The accompanying graph shows quantified cell migration-stimulating activity of each fragment peptide. This experiment shows that the HMGB1 fragment peptide (17-25) is the smallest fragment with migration-stimulating activity.

All synthetic peptides were found to have activity (FIG. 1B). The HMGB1 fragment peptide (17-25) was shown to be the smallest fragment that has the migration-stimulating activity.

Example 2

(Methods)

Seven-week-old female C57BL6/J mice were used as test animals. After the mice were anesthetized by isoflurane inhalation, skin incision was made along the dorsal midline, and the vertebral arch of the ninth thoracic vertebra was exposed and excised. Dura mater was exposed at the same site, and the spinal cord was held epidurally for three seconds using a microneedle holder to produce a traumatic injury of the spinal cord. After generation of injury of the spinal cord, the skin was sutured. Injury of the spinal cord was confirmed on the next day of operation by assessing paralysis of both hindlimbs, and mice that did not show paralysis were excluded from the assay. The assay reagent was prepared by diluting 100 µg of an HMGB1 fragment (amino acid sequence: amino acids of positions 11 to 44; synthesized peptide produced at MBL) in 200 µL of Dulbecco's PBS (D-PBS). 200 µL of D-PBS was used for the negative control. On the next day of operation, the first administration was performed through the tail vein, and this was followed by a total of five daily administrations. Neurologic symptoms were assessed using the Basso Mouse Scale (BMS) score on Days 1, 3, 7, 10, 14, 17, and 21 post operation.
(Results)

Figure 2A:
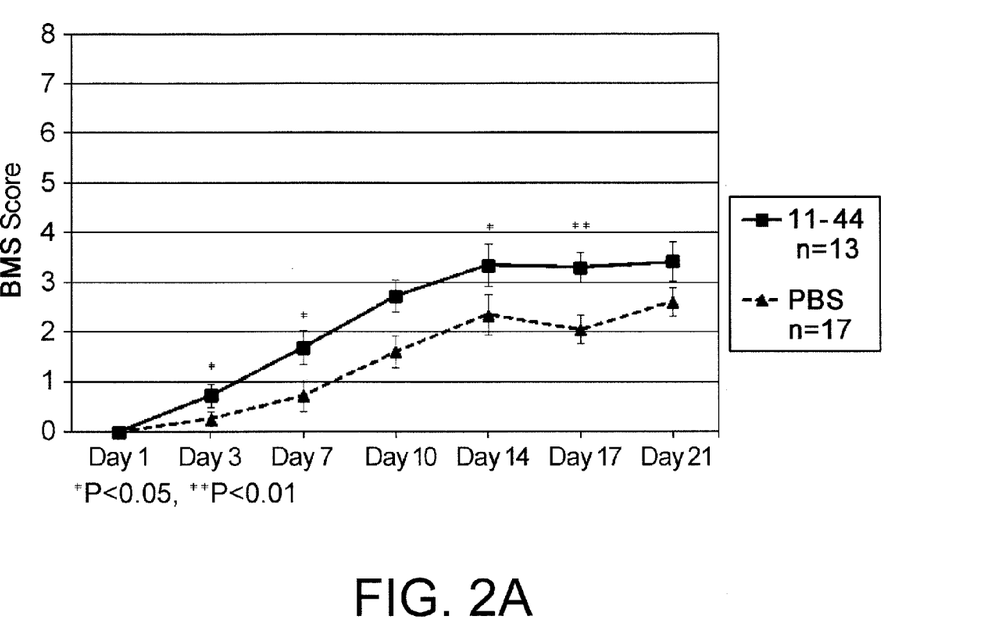
FIG. 2A shows that significant effects of improving neurologic symptoms were observed in the HMGB1 fragment (11-44)-administered group as compared to the negative control (PBS-administered) group. (*p<0.05, **p<0.01 VS. PBS)
Figure 2B:
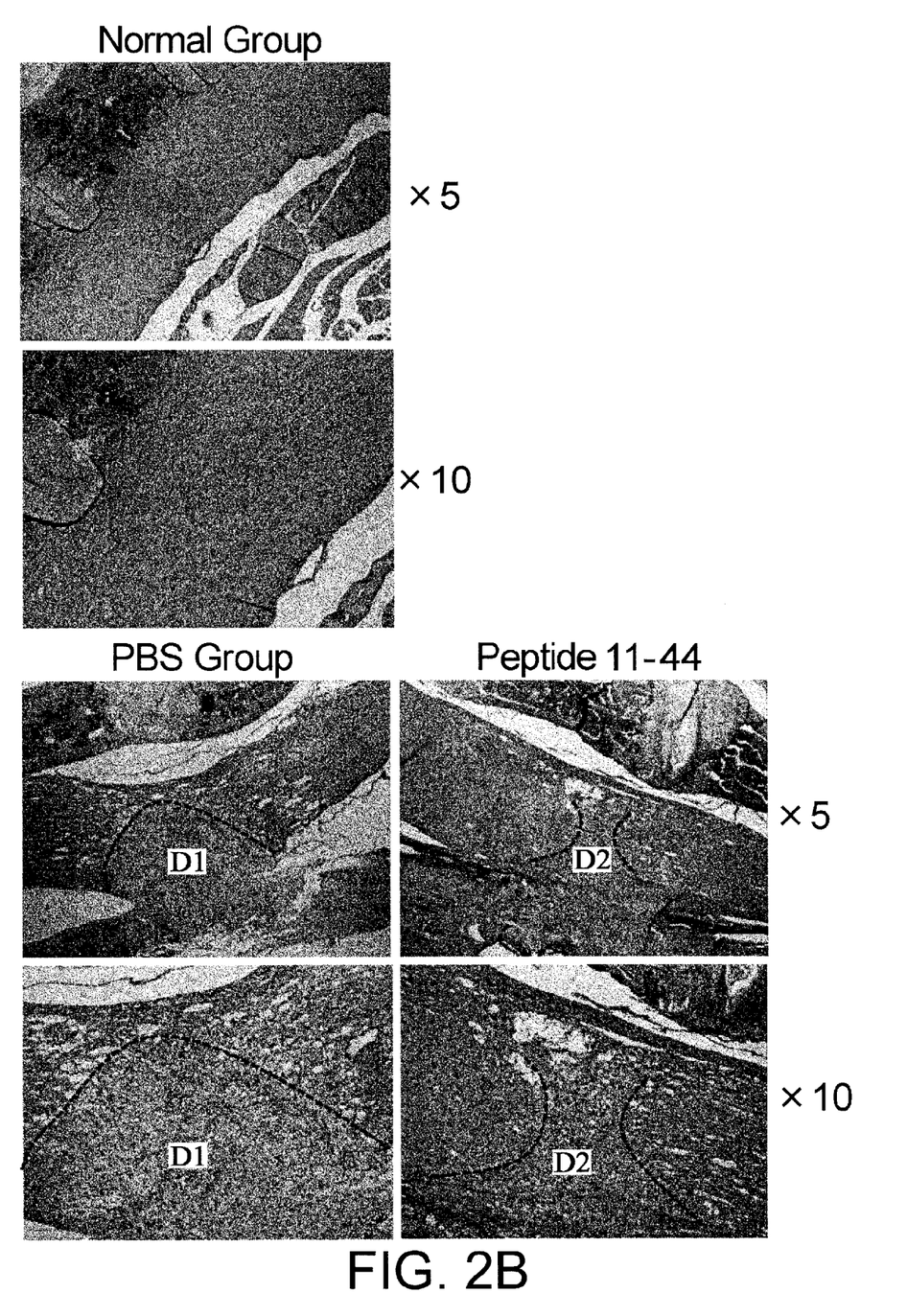

Based on the BMS scores, significant improvement of neurologic symptoms was observed from Day 3 post operation in the HMGB1 fragment-administered group as compared to the PBS-administered group. In particular, remarkable improvement of symptoms was observed on Days 3, 7, 14, and 17 post operation (FIG. 2A). Furthermore, while the HE staining images of the damaged region of the spinal cord for the negative control group showed damage in a wide range (D1), the damaged region (D2) for the HMGB1 fragment (11-44 peptide)-administered group was reduced, and therapeutic effects were observed histopathologically as well (FIG. 2B).

(Discussion)

Clear improvement of neurologic symptoms of mice inflicted with injury of the spinal cord was observed by HMGB1 fragment administration. Bone marrow mesenchymal stem cell-mobilizing activity has been found for the HMGB1 fragments used in this examination, and therapeutic effects of the mobilized bone marrow mesenchymal stem cells on injury of the spinal cord were expected. The effects of bone marrow mesenchymal stem cells on tissue damages are expected to be tissue regeneration through differentiation into nerve cells by pluripotency, as well as protective action of growth factors, cytokines, and such secreted by the bone marrow mesenchymal stem cells on damaged tissues. In the present assay, short-term effects up to the first week after the operation may be due to the latter action, and subsequently, the former action may be involved.

Example 3

(Methods)

Seven-week-old female C57BL6/J mice were used as test animals. After the mice were anesthetized by isoflurane inhalation, skin incision was made along the dorsal midline, and the vertebral arch of the ninth thoracic vertebra was exposed and excised. Dura mater was exposed at the same site, and the spinal cord was held epidurally for three seconds using a microneedle holder to produce a traumatic injury of the spinal cord. After production of injury of the spinal cord, the skin was sutured. Injury of the spinal cord was confirmed on the next day of operation by assessing paralysis of both hindlimbs, and mice that did not show paralysis were excluded from the assay. An HMGB1 fragment (amino acid sequence: the amino acids of positions 11 to 44; synthetic peptide produced at MBL) was prepared by diluting 100 μg of the fragment in 200 μL of Dulbecco's PBS (D-PBS). The full-length HMGB1 protein was produced by expressing it in HEK293 as reported previously, and the purified HMGB1 (100 μg) was dissolved in 200 μL of D-PBS. 200 μL of D-PBS was used for the negative control. On the next day of operation, the first administration was performed through the tail vein, and this was followed by a total of five daily administrations. Neurologic symptoms were assessed using the BMS score on Days 1, 3, 7, and 14 post operation.

(Results)

Figure 3:
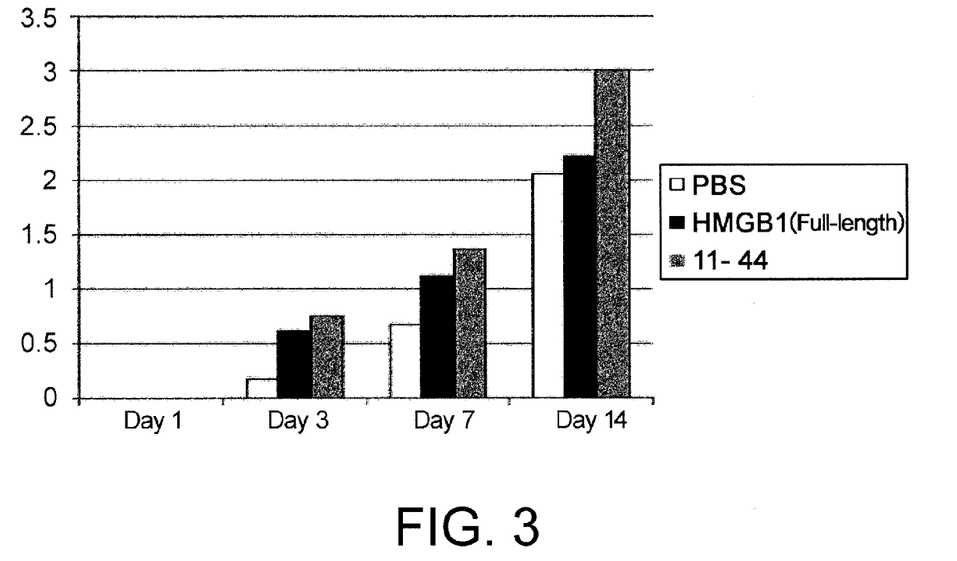
FIG. 3 is a graph that compares the full-length HMGB1-administered group and the HMGB1 fragment (11-44)-administered group for the effect of improving neurologic symptoms in disease model animals inflicted with injury of the spinal cord over time.

Effects on the improvement of neurologic symptoms were assessed using the BMS scores. The therapy was most effective in the HMGB1 fragment (amino acids at positions 11-44)-administered group on both Days 7 and 14. While the therapeutic effect was observed in the HMGB1 (full-length)-administered group when compared to that in the negative control group, it was not as effective as that in the HMGB1 fragment (amino acids at positions 11-44)-administered group (FIG. 3).

(Discussion)

After production of injury of the spinal cord, in the early stage, the therapeutic effect in the full-length HMGB1-administered group was found to be intermediate between the effect in the HMGB1 fragment (amino acids at positions 11-44)-administered group and that in the negative control group; however, by Day 14 post production of injury of the spinal cord, a much more satisfactory improvement of the therapeutic effect was observed in the HMGB1 fragment (amino acids at positions 11-44)-administered group than in other groups. These experiments revealed that rather than the full-length protein, the fragment shows greater therapeutic effects on injuries of the spinal cord. Peptides that can be chemically synthesized, such as this fragment, may be extremely useful in practical applications, since they allow production of inexpensive and homogenous products in large quantities in pharmaceutical production.

Example 4

Methods

Seven-week-old female C57BL6/J mice were used as test animals. The mice were anesthetized by isoflurane inhalation, skin incision was made along the dorsal midline, and the vertebral arch of the ninth thoracic vertebra was exposed and excised. Dura mater was exposed at the same site, and the spinal cord was held epidurally for three seconds using a microneedle holder to produce a traumatic injury of the spinal cord. After production of injury of the spinal cord, the skin was sutured. Injury of the spinal cord was confirmed on the next day of operation by assessing paralysis of both hindlimbs, and mice that did not show paralysis were excluded from the assay. HMGB1 fragments (amino acid sequences: amino acids from positions 11 to 44 and amino acids from positions 1 to 44; synthetic peptides produced at MBL) were prepared by diluting 100 μg of the fragment in 200 μL of D-PBS. 200 μL of D-PBS was used for the negative control. On the next day of operation, the first administration was performed via the tail vein, and this was followed by a total of five daily administrations. Neurologic symptoms were assessed using the BMS score on Days 1, 3, 7, 10, 14, 17, 21, and 28 post operation.

(Results)

Figure 4:
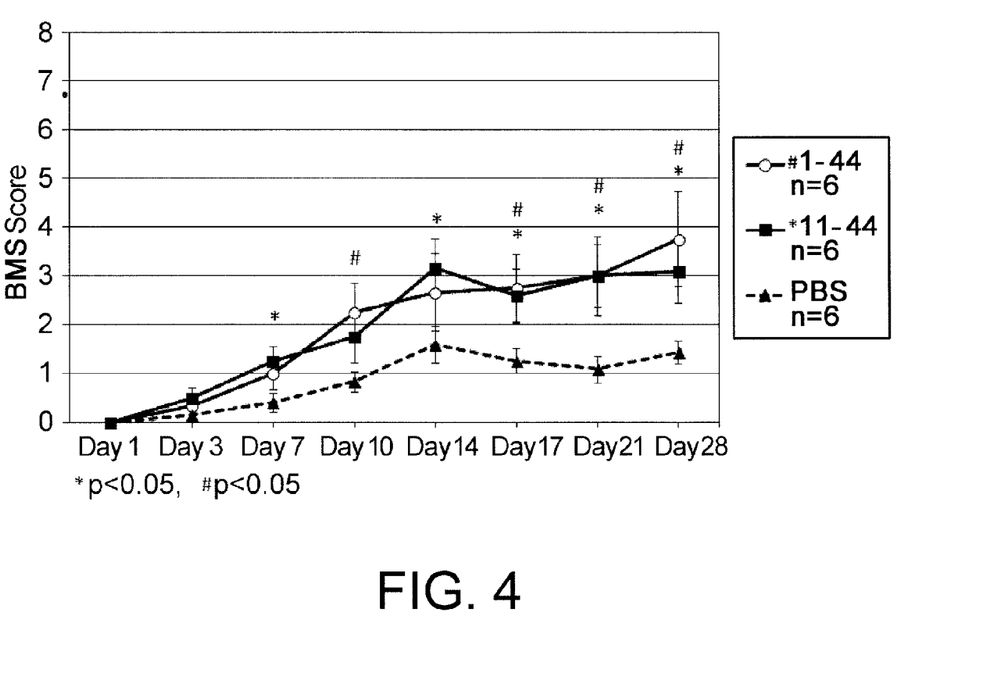
FIG. 4 is a graph that compares the HMGB1 fragment (11-44 and 1-44)-administered groups for the effect of improving neurologic symptoms in disease model animals inflicted with injury of the spinal cord. (#: 1-44, #p<0.05 VS. PBS; *: 11-44, *p<0.05 VS. PBS)

Effects on the improvement of neurologic symptoms were assessed using the BMS scores. In comparison to the negative control group, therapeutic effects were observed in the HMGB1 fragment (amino acids at positions 11-44 and amino acids at positions 1-44)-administered groups on Days 17, 21, and 28. The HMGB1 fragment consisting of the amino acids from positions 11 to 44 and the HMGB1 fragment consisting of the amino acids from positions 1 to 44 had comparable therapeutic effects (FIG. 4).

(Discussion)

HMGB1 fragments 11-44 and 1-44 were both found to be effective in treating injury of the spinal cord. As shown in FIG. 1, the present inventors elucidated that one of the core domains of HMGB1 for the activity of recruiting bone marrow mesenchymal stem cells is a peptide consisting of the amino acids from positions 17 to 25. Both the 11-44 fragment and the 1-44 fragment include positions 17 to 25, and the core peptide that exhibits efficacy of these peptides is predicted to be the sequence of positions 17 to 25. It has been reported that RAGE is not involved in the mobilization of bone marrow mesenchymal stem cells by the full-length HMGB1 protein (Tamai, 2011, PNAS; and such), and since there are no reports that the 11-44 fragment and the 1-44 fragment are ligands for a known receptor such as RAGE, these fragments are expected to target a receptor that is still unknown.

INDUSTRIAL APPLICABILITY

The present invention provides novel uses of HMGB1 fragment peptides that retain the activity of recruiting PDGFRα-positive cells for treating injury of the spinal cord. The HMGB1 fragment peptides of the present invention are fragment peptides with a molecular weight of about 20 percent or less of the full-length HMGB1 protein consisting of 215 amino acids. Such fragment peptides can be produced by chemical synthesis using peptide synthesizers, and are thus expected to improve purity, provide stable production, and reduce costs in the situation of producing peptides as pharmaceuticals.

Moreover, full-length HMGB1 is known to have an activity to bind to lipopolysaccharides (LPS) which are one type of endotoxin. Contamination of even a trace amount of LPS in pharmaceuticals causes fever and such, and often results in serious side effects. Thus, LPS contamination in pharmaceuticals is strictly regulated. As HMGB1 has affinity for LPS, it is difficult to completely eliminate LPS from pharmaceuticals contaminated therewith. However, making HMGB1 into peptides reduces its affinity to LPS, and thus it is expected to reduce LPS contamination in pharmaceuticals. Accordingly, by using an HMGB1 fragment comprising the portion for recruiting PDGFRα-positive cells as specified in the present invention, it is possible to develop safer pharmaceutical compositions for treating injury of the spinal cord.

Direct administration of the HMGB1 fragment of the present invention to the injury of spinal cord site in need of regeneration, or to the vicinity thereof, may induce or enhance regeneration of the lesion. Further, regeneration of injury of the spinal cord may be induced or enhanced by administering the HMGB1 fragment of the present invention to a site different from the site in need of regeneration by means such as intravenous administration. As such, the present invention enables treatment of injury of the spinal cord with intravenous administration, which is widely performed in general practice; and thus, therapeutic agents can be safely and easily administered at arbitrary concentrations for an arbitrary number of times. This fact is one of the extremely superior aspects of the present invention in comparison to conventional therapeutic methods.

In current practice of regenerative medicine or cell therapy, scarce bone marrow pluripotent stem cells derived from patients are cultured ex vivo and used for therapies after proliferation; however, since the culturing process carries the risk of cell deterioration (canceration or contamination of bacteria, viruses, and such), sufficient safety control is required. In contrast, therapeutic agents based on the present invention do not include the step of taking cells outside the body or the step of including manual operation, and thus, they are believed to be relatively safe. This fact is also one of the superior aspects of the present invention in comparison to conventional therapeutic methods.

The invention claimed is:

1. A method for treating injury or the spinal cord, comprising the step of administering a peptide that has an activity of stimulating the migration of mesenchymal stem cells, and comprises an amino acid sequence selected from the group consisting of SEQ ID NO: 3, SEQ ID NO: 4, and SEQ ID NO: 5.

2. A method for treating injury of the spinal cord, comprising the step of administering a peptide consisting of an amino acid sequence selected from the group consisting of SEQ ID NO: 3, SEQ ID NO: 4, and SEQ ID NO: 5.

* * * * *